(12) United States Patent
Boenig et al.

(10) Patent No.: US 8,585,681 B2
(45) Date of Patent: Nov. 19, 2013

(54) SYSTEMS AND METHODS FOR INCREASING STERILIZATION DURING PERITONEAL DIALYSIS

(75) Inventors: William Boenig, San Mateo, CA (US); Andy Katz-Mayfield, Santa Monica, CA (US); Zaafir Kherani, San Francisco, CA (US); Julia Rasooly, San Francisco, CA (US); Danielle Weiss, Carlsbad, CA (US)

(73) Assignee: PuraCath Medical, Inc., San Francisco, CA (US)

( * ) Notice: Subject to any disclaimer, the term of this patent is extended or adjusted under 35 U.S.C. 154(b) by 301 days.

(21) Appl. No.: 13/104,004

(22) Filed: May 9, 2011

(65) Prior Publication Data

US 2012/0116294 A1 May 10, 2012

Related U.S. Application Data

(60) Provisional application No. 61/333,250, filed on May 10, 2010, provisional application No. 61/396,827, filed on Jun. 3, 2010.

(51) Int. Cl.
*A61M 39/00* (2006.01)
(52) U.S. Cl.
USPC .......................................................... 604/533
(58) Field of Classification Search
USPC ..................................... 604/533; 250/455.11
See application file for complete search history.

(56) References Cited

U.S. PATENT DOCUMENTS

| | | | |
|---|---|---|---|
| 4,209,013 A | 6/1980 | Alexander et al. | |
| 4,242,310 A | 12/1980 | Greff et al. | |
| 4,346,704 A | 8/1982 | Kulle | |
| 4,412,834 A | 11/1983 | Kulin et al. | |
| 4,439,188 A | 3/1984 | Dennehey et al. | |
| 4,475,900 A | 10/1984 | Popovich et al. | |
| 4,503,333 A * | 3/1985 | Kulin et al. | 250/455.11 |
| 2007/0176117 A1 * | 8/2007 | Redmond et al. | 250/455.11 |
| 2011/0213339 A1 | 9/2011 | Bak | |
| 2012/0116294 A1 | 5/2012 | Boenig et al. | |

FOREIGN PATENT DOCUMENTS

WO 2008144437 A2 1/2008
WO 2009006506 A1 8/2009

OTHER PUBLICATIONS

Bak, J., et al., "Dose requirement for UVC disinfection of catheter biofilms," Biofouling: The Journal of Bioadhesion and Biofilm Research, vol. 25, No. 3, Apr. 2009, pp. 289-296, Taylor & Francis, London, England.

(Continued)

*Primary Examiner* — Kevin C Sirmons
*Assistant Examiner* — Deanna K Hall
(74) *Attorney, Agent, or Firm* — Fulwider Patton LLP

(57) ABSTRACT

A device for use in dialysis includes an elongated tubular body having a first end, a second end, and a lumen extending between the first end and the second end, and a first UV source coupled to the elongated tubular body at the second end, wherein the first UV source is configured to direct UV light for sterilizing at least a part of the elongated tubular body, wherein the second end of the elongated tubular body includes an opening in fluid communication with the lumen of the elongated tubular body, and a cover, the cover positionable at a first location to close the opening and at a second location to unblock the opening.

28 Claims, 6 Drawing Sheets

(56) References Cited

OTHER PUBLICATIONS

Bak, J., et al., "Disinfection of *Pseufomonas aeruginosa* biofilm contaminated tube lumens with ultraviolet C light emitting diodes," Biofouling: The Journal of Bioadhesion and Biofilm Research, vol. 26, No. 1, Jan. 2010, pp. 31-38, Taylor & Francis, London, England.

Bak, J., et al., "UVC fluencies of preventative treatment of *Pseudomonas aeruginosa* contaminated polymer tubes," Biofouling: The Journal of Bioadhesion and Biofilm Research, vol. 26, No. 7, Oct. 2010, pp. 821-828, Taylor & Francis, London, England.

Bak, J., et al., "Potential in vivo UVC idsinfection of catheter lumens: estimation of the doses received by the blood flow outside the catheter tip hole," Photochemistry and Photobiology, vol. 87, 2011, pp. 350-356, International.

\* cited by examiner

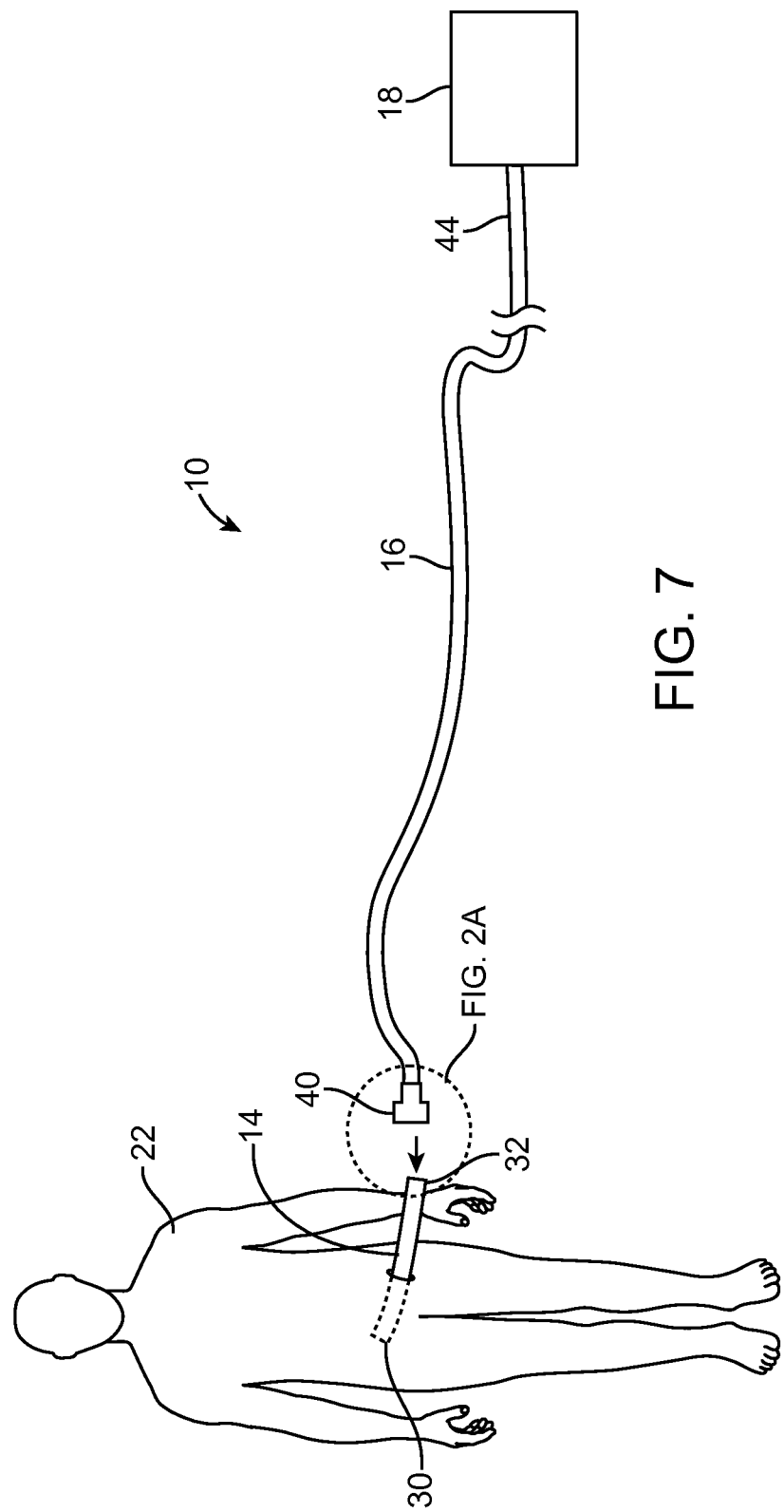

SYSTEMS AND METHODS FOR INCREASING STERILIZATION DURING PERITONEAL DIALYSIS

PRIORITY DATA

This application claims priority to and the benefit of U.S. Provisional Patent Application No. 61/333,250, filed on May 10, 2010, and U.S. Provisional Patent Application No. 61/396,827, filed on Jun. 3, 2010, the entire disclosures of all of which are expressly incorporated by reference herein.

FIELD

This application relates generally to dialysis, and more particularly, to peritoneal dialysis.

BACKGROUND

Peritoneal dialysis (PD) is a treatment for chronic kidney disease (CKD), a condition in which the kidneys fail to remove waste and excess water from the bloodstream. IN PD, dialysis solution enters the abdomen through an access site. After a few hours, the fluid becomes saturated with waste and is eventually drained through a catheter. There are two types of PD. Under continuous ambulatory peritoneal dialysis (CAPD), patients change fluid four times a day. Continuous cycling peritoneal dialysis (CCPD), on the other hand, occurs at night through a machine that drains and refills the abdomen automatically. Unlike most hemodialysis (HD) patients, PD patients perform dialysis themselves. The protocol for sterilization procedures for PD patients involves multiple steps and is highly susceptible to imperfections and to bacterial contamination at every step. Peritonitis infections are the leading cause for a PD patient to transfer to HD. The incidence of peritonitis is 0.27 episodes/patient year for CAPD patients, and 1.48/patient year for CCPD patients. The main bacterium that causes this peritonitis is *Staphylococcus aureus*, which is part of the normal flora of the skin. Treatment for peritonitis includes long-term antibiotic treatment that causes multiple side effects and does not always eradicate the infection.

However, PD has several advantages over hemodialysis including mobility, fewer dietary restrictions, less cardiovascular stress and better blood pressure. Its disadvantages are peritonitis, increased risk of back pain, loss of protein, and lower survival rates than HD after diagnosis of cardiovascular disease.

Applicant of the subject application determines that new devices and methods for preventing or reducing infections in dialysis would be desirable.

SUMMARY

In accordance with some embodiments, a device for use in dialysis includes an elongated tubular body having a first end, a second end, and a lumen extending between the first end and the second end, and a first UV source coupled to the elongated tubular body at the second end, wherein the first UV source is configured to direct UV light for sterilizing at least a part of the elongated tubular body, wherein the second end of the elongated tubular body includes an opening in fluid communication with the lumen of the elongated tubular body, and a cover, the cover positionable at a first location to close the opening and at a second location to unblock the opening.

In accordance with other embodiments, a device for use in dialysis includes a connector having a first end, a second end, and a lumen between the first end and the second end, and a catheter slidably disposed within the lumen of the connector, the catheter having a first catheter end for detachably coupling to an elongated tubular body through the connector, and a second catheter end for coupling to a dialysate bag, and a barrier having an adhesive surface facing away from the lumen of the connector.

Other and further aspects and features will be evident from reading the following detailed description of the embodiments.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

FIG. 7 illustrates another dialysis system for peritoneal dialysis in accordance with other embodiments.

DESCRIPTION OF THE EMBODIMENTS

Figure 1:
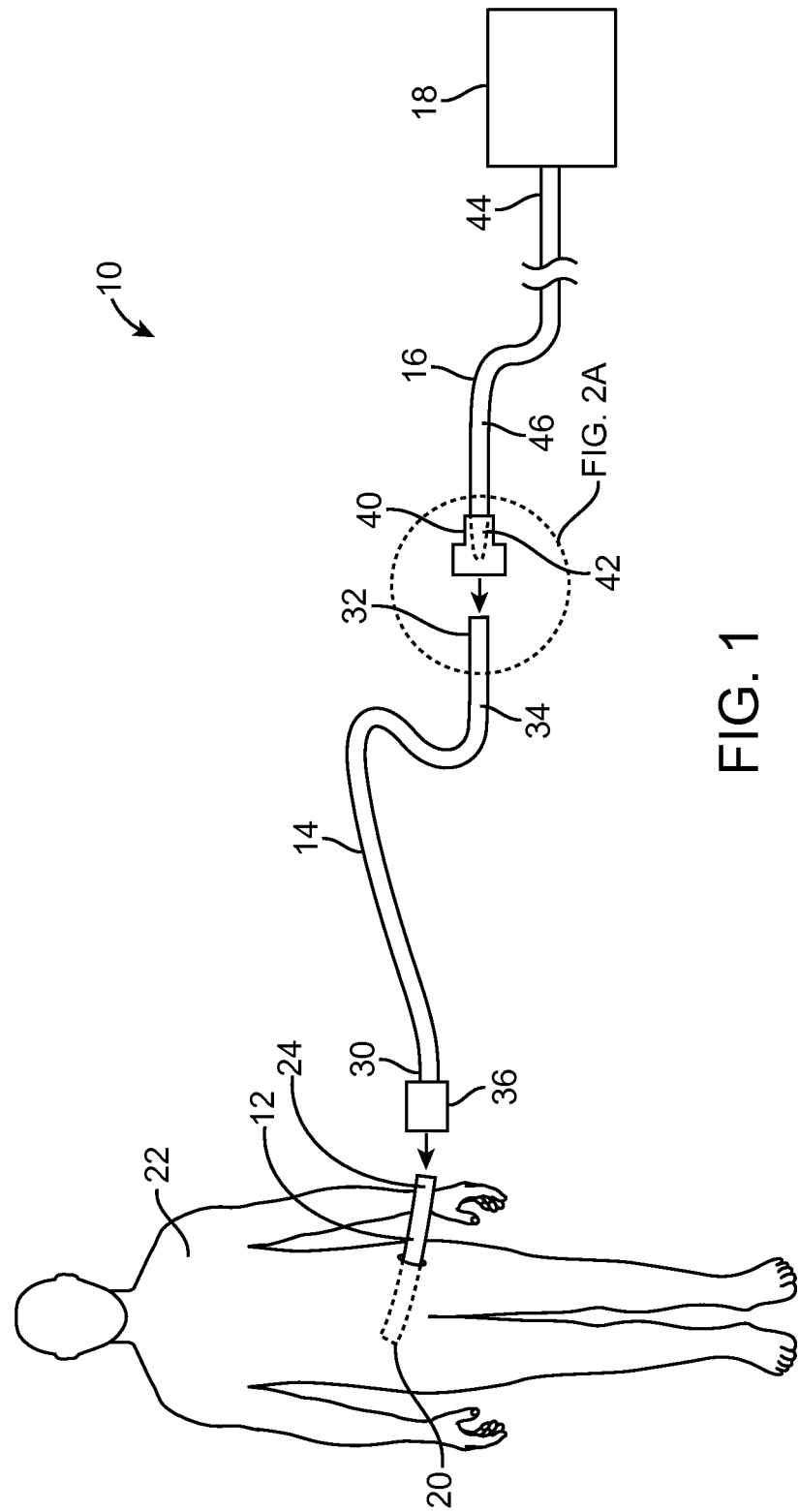
FIG. 1 illustrates a dialysis system for peritoneal dialysis in accordance with some embodiments, particularly showing the dialysis system having a tubular body and a catheter configured to detachably couple to an end of the tubular body.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 illustrates a peritoneal dialysis system 10 in accordance with some embodiments. The system 10 includes an implantable tube 12, an elongated tubular body 14, a catheter 16, and a dialysate bag 18. The implantable tube 12 includes a first end 20 for implant inside a patient 22, and a second end 22. The elongated tubular body 14 includes a first end 30 configured (e.g., sized and/or shaped) for detachably coupling to the second end 24 of the implantable tube 12 through a connector 36, a second end 32, and a lumen 34 between the first end 30 and second end 32. In some embodiments, the connector 36 may be considered to be a part of the elongated tubular body 14 (e.g., it may be considered to be a part of the first end 30). The catheter 16 includes a first end 42, a second end 44, and a lumen 46 between the first end 42 and the second end 44. The first end 42 of the catheter 16 is configured to detachably couple to the second end 34 of the elongated tubular body 14 through a connector 40. The second end 44 of the catheter 16 is configured to couple to the dialysate bag 18. The connector 40 may be considered to be a part of the system 10. In other embodiments, the connector 40 may be considered to be a part of the catheter 16 or a part of the elongated tubular body 14.

The tubular body 14 may have different lengths in different embodiments. In some embodiments, the tubular body 14 may have a length that is anywhere between 2 cm and 60 cm, and more preferably, anywhere between 5 cm and 40 cm. In other embodiments, the tubular body 14 may have a length that is longer than 40 cm.

Figure 2A:
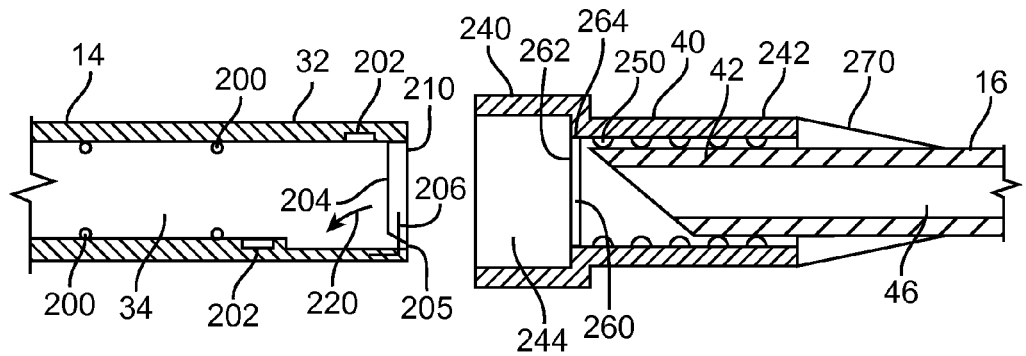
FIGS. 2A-2F illustrate parts of the dialysis system of FIG. 1, particularly, showing how the parts are used during a dialysis process.

FIG. 2A illustrate the elongated tubular body 14, the connector 40, and the catheter 16 in further detail. As shown in the figure, the second end 32 of the elongated tubular body includes a plurality of seals 200, two UV sources 202, a cover 204, and a hinge 206 for rotatably coupling the cover 204 relative to the elongated tubular body 14. In some embodiments, each seal 200 may be a rubber ring. Although two seals 200 are shown, in other embodiments, the elongated tubular body 14 may include one seal 200, or more than two seals 200. Each UV source 202 is configured to provide UV light for sterilizing at least part(s) of the system 10. The UV light may have a wavelength that is anywhere from 240 nm to 280 nm, and more preferably at 264 nm. In some cases, the UV light may have a wavelength range of 240-280 nm, with the peak efficiency at 264 nm. The UV sources 202 are located at the end 32 of the tubular body 14 and are close to the cover 204. In other embodiments, the UV sources 202 may be located anywhere else along the length of the tubular body 14. Although two UV sources 202 are shown, in other embodiments, the elongated tubular body 14 may include only one UV source 202, or more than two UV sources 202. The UV sources 202 are configured to provide UV light for sterilizing at least the distal end 32 of the elongated tubular body 14. The UV sources 202 are located at different respective locations along a longitudinal length of the elongated tubular body 14 so that at least a length of the elongated tubular body 14 may be sterilized by the UV lights from the UV sources 202. The UV sources 202 may be electrically coupled to one power source (e.g., battery or energy-storing capacitor) or respective power sources for energizing the UV sources 202. The power source(s) may be located outside the elongated tubular body 14, inside the lumen 34 of the tubular body 14, or inside a wall of the tubular body 14.

In the illustrated embodiments, the cover 204 is configured (e.g., sized, shaped, and/or positioned) to cover an opening 210 at the end 32 of the elongated tubular body 14 that is in fluid communication with the lumen 34 of the elongated tubular body 14. In some embodiments, a living hinge 205 (e.g., a plastic piece) may be used to connect the cover 204 to the rest of the tubular body 14. In other embodiments, the cover 204 may be coupled to the rest of the tubular body 14 using other mechanisms, such as a hinge shaft. In further embodiments, the living hinge 205 is optional, and the tubular body 14 does not include the living hinge 205. The hinge 206 is configured to rotatably couple the cover 204 relative to the elongated tubular body 14. The hinge 206 may be made from any elastic material, such as Nitinol, or any of other shape memory alloys. In the illustrated embodiments, the hinge 206 is in the form of a spring so that it urges the cover 204 to close the opening 210. The spring 206 may be a torsional spring in some embodiments. Alternatively, the spring 206 may be an elastic strip with a bent configuration. During use, the cover 204 may be pressed to swing open in the direction of the arrow 220 in response to a force or pressure applied thereto, while the spring 206 acts as a hinge. The spring 206 provides a force to urge the cover 204 to close the opening 210, such that when the force or pressure applied to the cover 204 is removed, the cover 204 will spring back to its closed configuration. In some embodiments, the cover 204 may be made from the same material as that of the tubular body 14. In other embodiments, the cover 204 may be made from a different material (e.g., a stiffer material) from that of the tubular body 14.

The connector 40 includes a first end 240 for detachably coupling to the end 32 of the tubular body 14, a second end 242, and a lumen 244 between the first end 240 and the second end 242. The catheter 16 is slidably disposed within the lumen 244 of the connector 40. The connector 40 further includes a plurality of seals 250 that interface between the catheter 16 and the connector 40. In some embodiments, each seal 250 may be a rubber ring. The seals 250 allow the catheter 16 to slide relative to the connector 40, while preventing fluid from escaping through the space between the catheter 16 and the connector 40. In other embodiments, instead of having a plurality of seals 250, the connector 40 may include only one seal 250. In further embodiments, the connector 40 may not include any seal. In such cases, the catheter 16 may be configured (e.g., sized and/or shaped) to frictionally engage with an interior wall of the connector 40.

As shown in FIG. 2A, the connector 40 further includes a barrier 260 with an adhesive surface 262. The barrier 260 is aligned with a longitudinal axis of the connector 40 so that when the connector 40 is detachably coupled to the tubular body 14, the adhesive surface 262 of the barrier 260 will engage with the cover 204, and will adhere the barrier 260 to the cover 204. In some embodiments, the adhesive surface 262 may include an adhesive (like that of a tape). In other embodiments, the adhesive surface 262 may be implemented using a magnet. In some embodiments, the barrier 260 may be made from a plastic or a polymer. Also, in some embodiments, the barrier 260 may be detachably connected to the connector 40 at location 264. During use, the catheter 16 may slide distally relative to the connector 40 to push the barrier 260 against the cover 204. Also, further distal movement of the catheter 16 relative to the connector 40 may detach the barrier 260 from the connector 40 at the location 264.

In other embodiments, the connector 40 may optionally further include a circumferential protrusion that extends from an interior wall. In such cases, the side of the barrier 260 opposite from the adhesive surface may be rested against the circumferential protrusion, and may be detachably attached to the circumferential protrusion via an adhesive. During use, the circumferential protrusion may be used to push the barrier 260 towards the cover 204, and the catheter 16 may be used to detach the barrier 260 from the circumferential protrusion by advancing the catheter 16 distally relative to the connector 40.

In any of the embodiments described herein, the system 10 may further include a connecting element 270 for tying the connector 40 to the catheter 16 so that the two components would not be completely separated. This has the benefit of preventing the connector 40 from unintentionally being separated from the catheter 16 and getting lost. The connecting element 270 may be a string, a strap, etc.

In some embodiments, the connector 40, the catheter 16, the dialysate bag 18, and the barrier 260 are disposable. In such cases, a kit may be provided that include multiple sets of disposable unit, wherein each set of disposable unit will include the connector 40, the catheter 16, the dialysate bag 18, and the barrier 260.

Figure 2B:
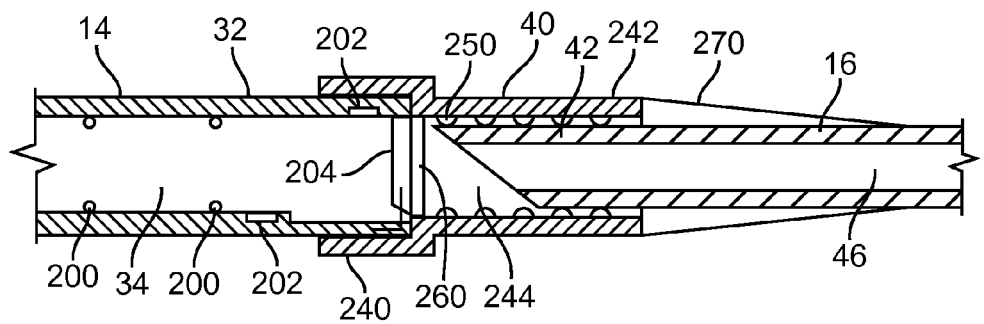

FIGS. 1 and 2B-2F illustrate how a dialysis process may be performed using the system 10 in accordance with some embodiments. First, the elongated tubular body 14 is detachably coupled to the implantable tube 12 through the connector 36 at the first end 30 (FIG. 1). Next, the first end 240 of the connector 40 is detachably coupled to the second end 32 of the tubular body 14 (FIG. 2B). As shown in the figure, the end 32 of the tubular body 14 is inserted into the lumen 244 of the connector 40. At this stage, the cover 204 remains closed. When the connector 40 is coupled to the tubular body 14, the adhesive surface 262 of the barrier 260 engages with the cover 204, and secures the barrier 260 relative to the cover 204. Then, the UV sources 202 are activated to emit UV lights for sterilizing the distal end 32 of the elongated tubular body 14. Alternatively, the UV sources 202 may not be activated until the cover 204 is opened by the catheter 16 (as discussed below). In further embodiments, the UV sources 202 may be activated both before the cover 204 is opened, and after the cover 204 is opened. Such configuration ensures that the lumen 34 is sterilized first, and then the catheter 16 is sterilized.

Figure 2C:
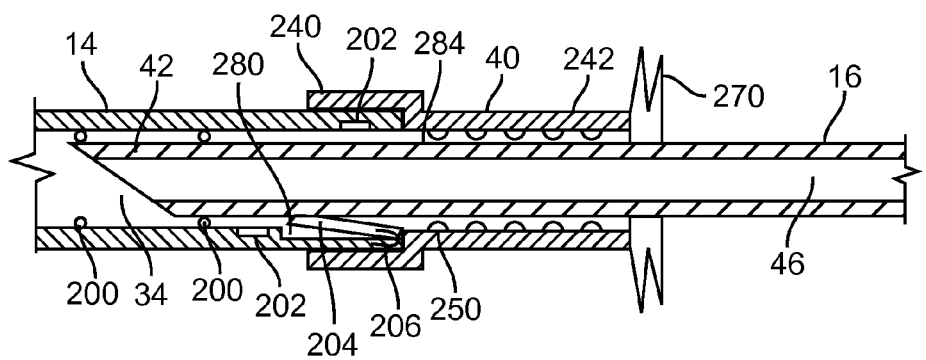

Next, the catheter 16 may be advanced distally relative to the connector 40 by pushing the catheter 16 distally relative to the connector 40 (and relative to the elongated tube 14) (FIG. 2C). When the catheter 16 initially engages with the barrier 260, the catheter 16 may impose force against the barrier 260 so that the barrier 260 is pressed against the cover 204. This ensures that the barrier 260 is adequately secured to the cover 204 via the adhesive surface 262. When the catheter 16 is further advanced distally, the advancement force of the catheter 16 may break the bond between the barrier 260 and the connector 40 at the location 264, thereby allowing the barrier 260 to move together with the cover 204. In particular, the further advancement of the catheter 16 will push open the cover 204, allowing the distal end 42 of the catheter 16 to enter into the lumen 34 of the tubular body 14 (FIG. 2C). As shown in the figure, the tubular body 14 may optionally further include a recess 280 for accommodating at least a part of the cover 204 after the cover 204 is positioned to its open configuration.

After the catheter 16 has opened the cover 204, the UV sources 202 may be activated to sterilize the tubular body 14 and/or the catheter 16. The UV sources 202 may be activated for a prescribed duration (e.g., at least 2 seconds) to provide an effective sterilization. As shown in the figure, the UV sources 202 are located on opposite sides inside the lumen 34. Such configuration is advantageous because it ensures that UV lights are provided on both sides of the catheter 16 to sterilize the entire circumference of the catheter 16. In some embodiments, the activation of the UV sources 202 may be performed manually by a user pressing a control button (which may be located on an exterior surface of the tubular body 14). In other embodiments, the activation of the UV sources 202 may be performed automatically in response to the opening of the cover 204. For example, the tubular body 14 may include a sensor for sensing an opening of the cover 204. In such cases, the sensor may send a signal to activate the UV sources 202 when it senses that the cover 204 has been desirably opened.

Next, fluid (a sterile solution containing glucose) from the dialysate bag 18 is delivered to the patient 22 through the catheter 16, the tubular body 14, and the implanted tube 12. While fluid is being delivered, the seals 200 at the tubular body 14 prevent fluid from escaping through the space between the catheter 16 and the tubular body 14, and the seals 250 at the connector 40 prevents fluid from escaping through the space between the catheter 16 and the connector 40.

The fluid from the dialysate bag 18 is delivered into the peritoneal cavity (the abdominal body cavity around the intestine), where the peritoneal membrane acts as a semipermeable membrane. The peritoneal membrane or peritoneum is a layer of tissue containing blood vessels that lines the peritoneal, or abdominal, cavity and the internal abdominal organs (including the stomach, spleen, liver, and intestines). The dialysate is left there for a period of time to absorb waste products from the patient 22, and then it is drained out through the implanted tube 12. This cycle or "exchange" may be repeated 4-5 times (or more often with an automated system) per day.

Figure 2D:
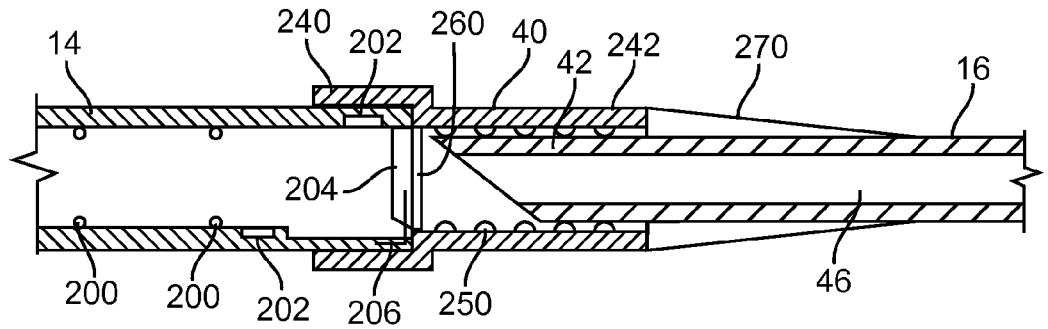
Figure 2E:
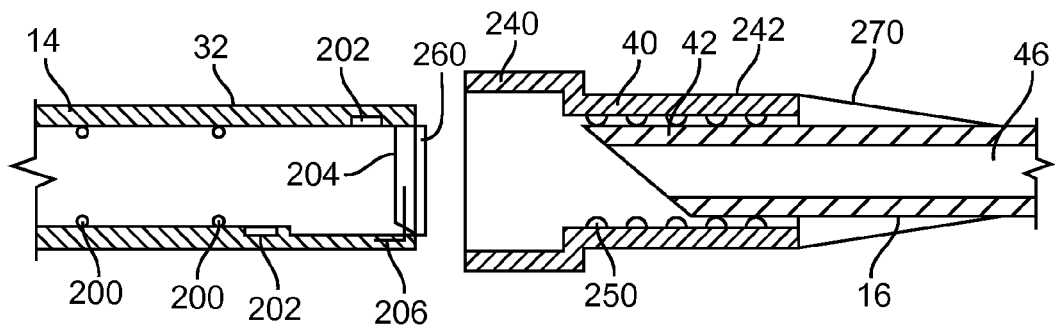
Figure 2F:
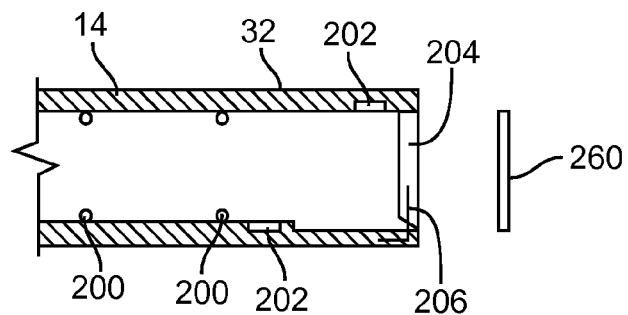

When the dialysis process is finished, the catheter 16 may be retracted proximally relative to the connector 40, thereby allowing the cover 204 to automatically close the opening 210 in response to the spring force applied by the spring 206 to seal the end of the tubular body 14 (FIG. 2D). The connector 40 is then decoupled from the tubular body 14 (FIG. 2E). In some embodiments, the connector 40, the catheter 16, and the dialysate bag 18 are for one-time use, and are disposed after the connector 40 and the catheter 16 are decoupled from the tubular body 14. Next, the barrier 260 may be removed from the cover 204 (e.g., by pulling it off to detach the bonding between the adhesive surface 262 and the cover 204) (FIG. 2F). Optionally, the UV sources 202 may then be activated to sterilize the distal end 32 of the tubular body 14, so that the tubular body 14 may be re-use later (e.g., in future dialysis processes).

As illustrated in the above embodiments, the system 10 is advantageous because it allows two tubes (i.e., the tubular body 14 and the catheter 16) to be coupled together in a way as to provide sterility of the respective lumens. The barrier 260 is beneficial because it maintains sterility of the cover 204 during the dialysis process, while the catheter 16 is being disconnected from the tubular body 14, and after the catheter 16 has been disconnected from the tubular body 14. This allows the tubular body 14 to be re-use.

Figure 3A:
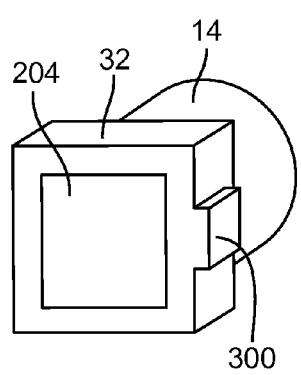
FIGS. 3A-3C illustrate a variation of an end of the tubular body of FIG. 1 in accordance with other embodiments.
Figure 3B:
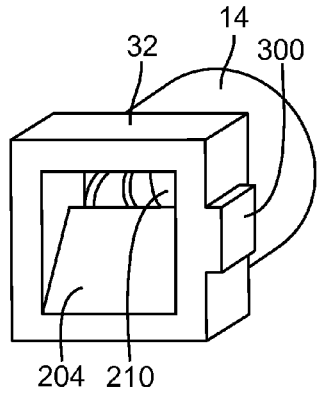
Figure 3C:
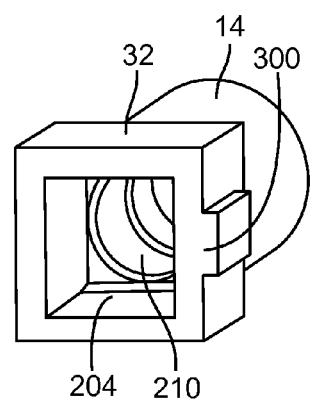
Figure 4A:
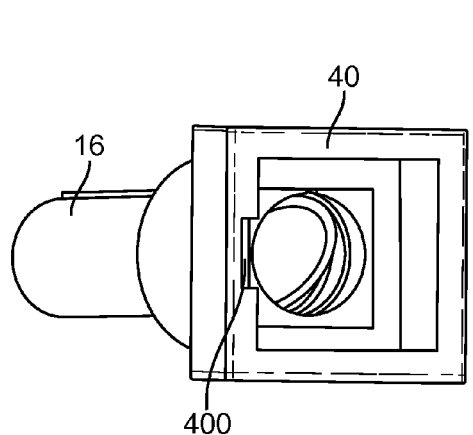
FIGS. 4A-4B illustrate a variation of an end of the catheter of FIG. 1 in accordance with other embodiments.
Figure 4B:
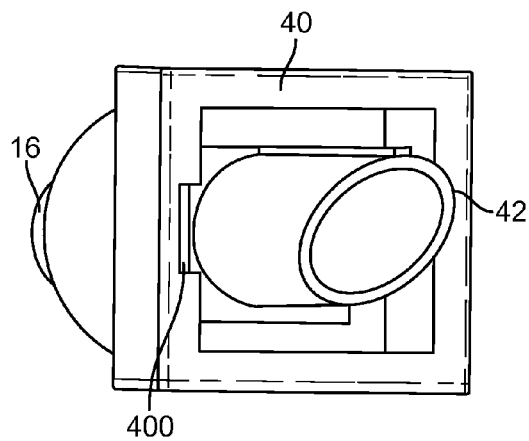

In any of the embodiments described herein the tubular body 14 may have a circular cross section, a square cross section, or cross section with other shapes. Also, in some embodiments, the end 32 of the tubular body 14 may have a cross sectional shape that is different from the rest (e.g., the majority of the length) of the tubular body 14. For example, in other embodiments, the end 32 of the tubular body 14 may have a square cross section (FIGS. 3A-3B). FIG. 3A illustrates the cover 204 in its closed configuration. FIG. 3B illustrates the cover 204 being partially opened. FIG. 3C illustrates the cover 204 being fully opened to uncover the opening 210. In some embodiments, the part of the tubular body 14 that mates with the connector 40 may be formed together with the rest of the tubular body 14 during a manufacturing process (e.g., through a molding process). In other embodiments, a separate component may be attached to a tube (e.g., via glue, mechanical connector, etc.) to form the end 32 of the tubular body 14. In the illustrated embodiments, the end 32 of the tubular body 14 may optionally include a key 300 for mating with a corresponding slot 400 (shown in FIGS. 4A-4B) at the connector 40. The key 300 and slot 400 are advantageous because they ensure that the tubular body 14 and the connector 40 (and the catheter 16) are detachably coupled to each other at the desired orientation. In other embodiments, instead of having one set of key-to-slot arrangement, the system 10 may include a plurality of key-to-slot arrangements. Also, in other embodiments, one or both of the tubular body 14 and the catheter 16 may have a circular cross section along a majority of the length, and the circular cross section gradually change to a rectangular cross section at the connection region. In some embodiments, the gradual change may span 2 cm or more.

Figure 5:
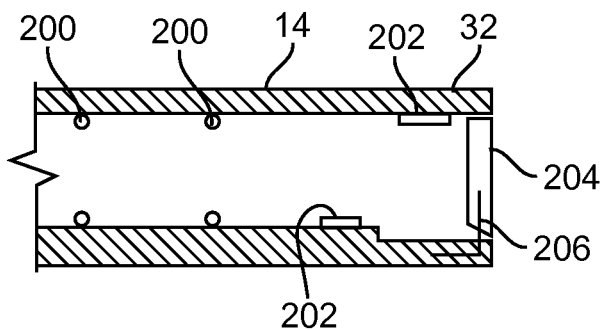
FIG. 5 illustrates another tubular body in accordance with other embodiments, particularly showing ultraviolet light (UV) sources attached to an interior wall of the tubular body.
Figure 6:
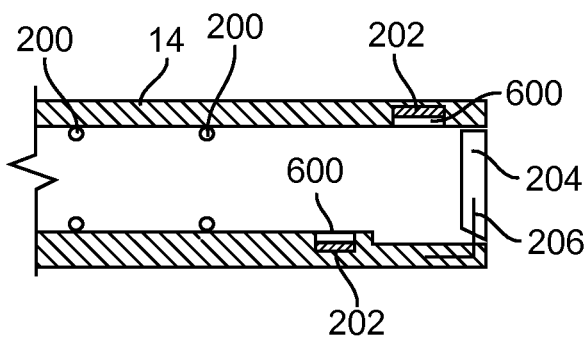
FIG. 6 illustrates another tubular body in accordance with other embodiments, particularly showing UV sources embedded inside a wall of the tubular body.

In the above embodiments, the UV sources 202 are illustrated as being partially embedded in a wall of the elongated tubular body 14. In other embodiments, the UV sources 202 may be secured to an interior surface of the elongated tubular body 14 (FIG. 5). In further embodiments, the UV sources 202 may be completely embedded in the wall of the elongated tubular body 14 (FIG. 6). In such cases, the elongated tubular body 14 may include windows 600 for allowing UV light from the UV sources 202 to transmit therethrough. Alternatively, the wall of the elongated tubular body 14 may be made from a material that is at least partially transparent to the UV light from the UV sources 202.

Also, in the above embodiments, the system 10 has been described as having the elongated tubular body 14 that couples between the implantable tube 12 and the catheter 16. In other embodiments, the elongated tubular body 14 may be an implantable tube itself. In such cases, the tubular body 14 does not include the connector 36. Instead, the end 30 of the tubular body 14 is configured for implant inside the patient 22 (FIG. 7).

In any of the embodiments described herein, the spring 206 at the tubular body 14 may not be included. In such cases, the catheter 14 may have a feature (e.g., a hook, a connector, etc.) that couples to the cover 204, such that when the catheter 14 is retracted proximally, the catheter 14 will pull the cover 204 to its closed configuration.

Also, in any of the embodiments described herein, the tubular body 14 may optionally further include a protrusion at the inner side of the cover 204, and an opening through a wall of the tubular body 14. In such cases, when the cover 204 is pushed open by the catheter 14, at least a part of the protrusion at the inner side of the cover 204 will extend through the opening at the wall of the tubular body 14. This will indicate to the user that the cover 204 has been desirably opened by the catheter 14. In other embodiments, the tubular body 14 may include a sensor for sensing an opening of the cover 204, and for sending out a signal (e.g., a visual signal, audio signal, or both) to inform the user that the cover 204 has been desirably opened.

In any of the embodiments described herein, the system 10 may further be configured to apply a negative pressure to the target site using a suction device, which would decrease the incidence of infection that occurs right around the target site. The suction device may be coupled to the second end 32 of the tubular body 14, the second end 44 of the catheter 16, or to the second end 24 of the implanted tube 12.

Also, in any of the embodiments described herein, the second end 32 of the tubular body 14 may include a heat releasing element for providing heat to kill temperature sensitive infectious agents. In such cases, the first end 30 of the tubular body 14 may be made from a material that absorbs heat so that fluid passing that region will be at an appropriate temperature.

Furthermore, in any of the embodiments described herein, at least a section (e.g., a majority of the length) of the tubular body 14 may include two concentric tubes. The outer tube may include or filled with an antimicrobial agent that diffuses into the inner tube at a fixed rate defined by the inner tube's material properties. The antimicrobial agent would kill infectious agents in the fluid.

Although the above embodiments have been described with reference to peritoneal dialysis, in other embodiments, the system 10 and technique described herein may be used to perform other types of dialysis.

Although particular embodiments have been shown and described, it will be understood that they are not intended to limit the claimed inventions, and it will be obvious to those skilled in the art that various changes and modifications may be made without departing from the spirit and scope of the claimed inventions. For example, in other embodiments, the UV sources 202 are optional, and the system 10 may not include any UV source. The specification and drawings are, accordingly, to be regarded in an illustrative rather than restrictive sense. The claimed inventions are intended to cover alternatives, modifications, and equivalents.

What is claimed:

1. A device for use in dialysis, comprising:
   an elongated tubular body having a first end, a second end, and a lumen extending between the first end and the second end; and
   a first UV source coupled to the elongated tubular body at the second end, wherein the first UV source is configured to direct UV light for sterilizing at least a part of the elongated tubular body;
   wherein the second end of the elongated tubular body includes an opening in fluid communication with the lumen of the elongated tubular body, and a cover, the cover positionable at a first location to close the opening and at a second location to unblock the opening and;
   further comprising a plastic piece having an adhesive surface for detachably coupling to the cover.

2. The device of claim 1, further comprising a second UV source coupled to the elongated tubular body.

3. The device of claim 2, wherein the first UV source and the second UV source are located at different respective locations along a length of the elongated tubular body.

4. The device of claim 1, further comprising an energy source coupled to the elongated tubular body for energizing the first UV source.

5. The device of claim 4, wherein one or both of the first UV source and the energy source are at least partially embedded within a wall of the elongated tubular body.

6. The device of claim 1, wherein the cover is rotatably coupled to the second end of the elongated tubular body.

7. The device of claim 1, further comprising a spring for urging the cover to close the opening, wherein the spring comprises a shape-memory alloy.

8. The device of claim 1, further comprising a spring for urging the cover to close the opening, wherein the spring comprises Nitinol.

9. The device of claim 1, wherein the second end of the elongated tubular body includes a connection component configured for detachably coupling to a connector, and wherein the opening and the door are located at the connection component.

10. The device of claim 1, further comprising:
    a connector; and
    a catheter having a first catheter end for detachably coupling to the second end of the elongated tubular body through the connector, and a second catheter end for coupling to a dialysate bag.

11. The device of claim 10, wherein the connector includes a tubular wall defining a lumen, and the catheter is slidable within the lumen of the connector.

12. The device of claim 11, wherein the connector further includes one or more seals coupled to an interior surface of the tubular wall.

13. The device of claim 10, further comprising the dialysate bag.

14. The device of claim 1, wherein the first end of the elongated tubular body is configured for coupling to an implantable tube.

15. The device of claim 1, wherein the first end of the elongated tubular body is configured for implant inside a body.

16. The device of claim 1, wherein the UV source is configured to activate automatically.

17. The device of claim 16, wherein the UV source is configured to activate automatically in response to a movement of the cover.

18. The device of claim 1, wherein the UV source is configured to provide a UV light having a wavelength that is anywhere from 240 nm to 280 nm.

19. A device for use in dialysis, comprising:
 a connector having a first end, a second end, and a lumen between the first end and the second end; and
 a catheter slidably disposed within the lumen of the connector, the catheter having a first catheter end for detachably coupling to an elongated tubular body through the connector, and a second catheter end for coupling to a dialysate bag; and
 a barrier having an adhesive surface facing away from the lumen of the connector.

20. The device of claim 19, wherein the connector further includes one or more seals coupled to an interior surface of the tubular wall.

21. The device of claim 19, further comprising the dialysate bag.

22. The device of claim 19, wherein the first catheter end has a sharp tip.

23. The device of claim 19, further comprising the elongated tubular body, wherein the elongated tubular body includes a first end, and a second end for detachably coupling to the catheter through the connector.

24. The device of claim 23, wherein the second end of the elongated tubular body includes an opening and a cover next to the opening, and wherein the barrier is aligned with a longitudinal axis of the connector so that when the connector is detachably coupled to the second end of the elongated tubular body, the adhesive surface of the barrier is detachably secured to the cover.

25. The device of claim 24, further comprising a UV source that is configured to automatically activate.

26. The device of claim 25, wherein the UV source is configured to automatically activate in response to a movement of the cover.

27. The device of claim 23, wherein the elongated tubular body includes a first UV source on a first side of the elongated tubular body, and a second UV source on a second side of the elongated tubular body that is opposite from the first side.

28. The device of claim 23, wherein the first end is configured for detachably coupling to an implantable tube.

* * * * *